United States Patent
Homs Corbera et al.

(10) Patent No.: US 12,241,052 B2
(45) Date of Patent: Mar. 4, 2025

(54) METHOD FOR GAS ENRICHMENT AND SIMULTANEOUSLY FOR DISPLACEMENT OF A FLUID, AND SYSTEM FOR CONTROLLING THE CELL ENVIRONMENT ON A CORRESPONDING MULTI-WELL CELL CULTURE PLATE

(71) Applicant: CHERRY BIOTECH, Montreuil (FR)

(72) Inventors: Antoni Homs Corbera, Sant Feliu de Guixols (ES); Matteo Boninsegna, Prato (IT); Theo Vital, Rennes (FR)

(73) Assignee: CHERRY BIOTECH, Montreuil (FR)

( * ) Notice: Subject to any disclaimer, the term of this patent is extended or adjusted under 35 U.S.C. 154(b) by 4 days.

(21) Appl. No.: 18/162,198

(22) Filed: Jan. 31, 2023

(65) Prior Publication Data

US 2023/0174919 A1 Jun. 8, 2023

Related U.S. Application Data

(62) Division of application No. 16/824,074, filed on Mar. 19, 2020, now Pat. No. 11,643,632.

(30) Foreign Application Priority Data

Mar. 20, 2019 (FR) ...................................... 1902859

(51) Int. Cl.
*C12M 1/34* (2006.01)
*B01L 3/00* (2006.01)
(Continued)

(52) U.S. Cl.
CPC ....... *C12M 41/40* (2013.01); *B01L 3/502715* (2013.01); *C12M 23/12* (2013.01);
(Continued)

(58) Field of Classification Search
CPC ...... C12M 41/40; C12M 23/12; C12M 27/00; C12M 29/06; B01L 3/502715; B01L 2300/047; B01L 2300/0829
See application file for complete search history.

(56) References Cited

U.S. PATENT DOCUMENTS

| 5,081,035 A | 1/1992 | Halberstadt et al. |
| 5,316,905 A | 5/1994 | Mori et al. |
| 11,643,632 B2 * | 5/2023 | Homs Corbera ...... C12M 29/14 435/354 |

(Continued)

FOREIGN PATENT DOCUMENTS

| EP | 0263634 A2 | 4/1988 |
| EP | 2623587 A1 | 8/2013 |

(Continued)

OTHER PUBLICATIONS

French Search Report and Written Opinion dated Nov. 11, 2019 for corresponding French Application No. 1902859, filed Mar. 20, 2019.

(Continued)

*Primary Examiner* — Brian J. Sines
(74) *Attorney, Agent, or Firm* — David D. Brush; Westman, Champlin & Koehler, P.A.

(57) ABSTRACT

A method for displacing a fluid and simultaneously gas enriching a liquid cell culture medium with a gas. The method includes injecting a controlled volume of a gas or gas mixture into a one chamber by using a gas flow controller, the injection taking place through a gas inlet into a volume of liquid. This injection produces bubbling and agitation of the volume of liquid; a build-up of gas or gas mixture due to buoyancy in a hermetic space formed by the volume of liquid and the chamber, and a pressure increase in the chamber until a sufficient controlled pressure is reached of less than or equal to 10 bar. This increase displaces the volume of liquid by a fluid outlet connecting the volume of liquid to the exterior of the chamber. Also provided are a device implementing the method and a cell culture system in a multi-well culture plate.

15 Claims, 4 Drawing Sheets

(51) Int. Cl.
*C12M 1/00* (2006.01)
*C12M 1/02* (2006.01)
*C12M 1/32* (2006.01)
*C12M 3/06* (2006.01)

(52) U.S. Cl.
CPC ............ *C12M 23/16* (2013.01); *C12M 27/00* (2013.01); *C12M 29/06* (2013.01); *B01L 2300/047* (2013.01); *B01L 2300/0829* (2013.01)

(56) References Cited

U.S. PATENT DOCUMENTS

2001/0021529 A1  9/2001  Takagi
2013/0203106 A1  8/2013  Shvets et al.

FOREIGN PATENT DOCUMENTS

WO  2004027016 A1  4/2004
WO  2007092571 A2  8/2007
WO  2009089189 A2  7/2009
WO  2018013646 A1  1/2018
WO  2018136752 A2  7/2018

OTHER PUBLICATIONS

European Search Report and Written Opinion including English translation dated Aug. 20, 2020 for corresponding European Application No. 20163255.1.

Notice of Allowance dated Jan. 5, 2023 for corresponding U.S. Appl. No. 16/824,074, filed Mar. 19, 2020.

* cited by examiner

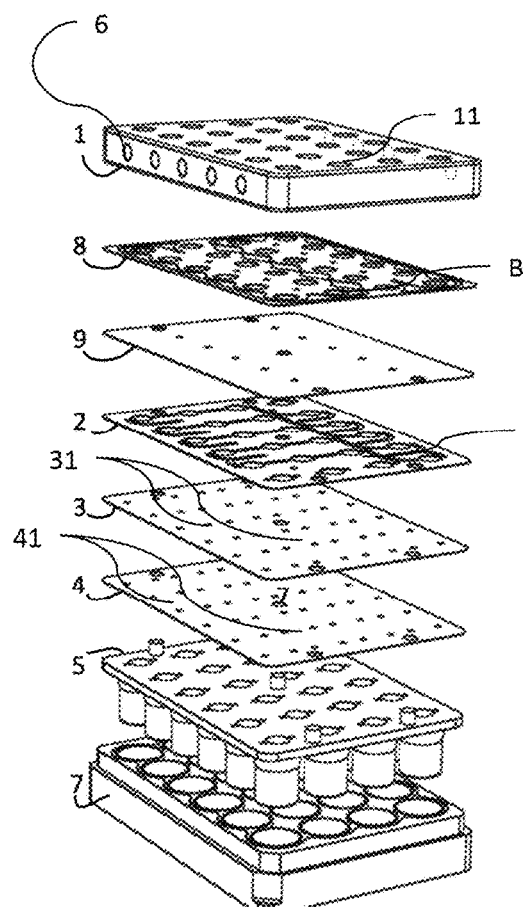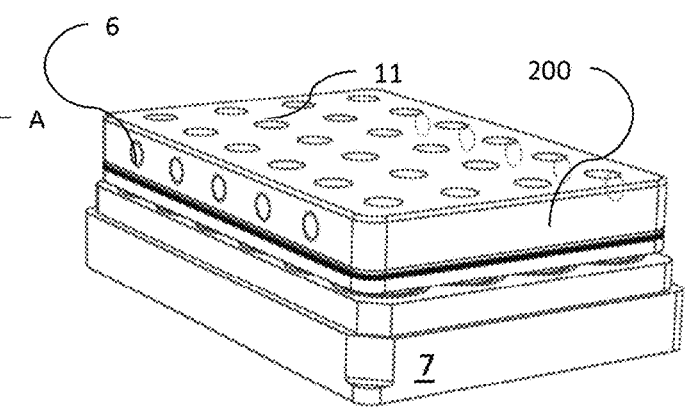
FIG.4A
FIG.4B

METHOD FOR GAS ENRICHMENT AND SIMULTANEOUSLY FOR DISPLACEMENT OF A FLUID, AND SYSTEM FOR CONTROLLING THE CELL ENVIRONMENT ON A CORRESPONDING MULTI- WELL CELL CULTURE PLATE

CROSS-REFERENCE TO RELATED APPLICATION

This application is a division of U.S. patent application Ser. No. 16/824,074, filed Mar. 19, 2020, the content of which is incorporated herein by reference in its entirety.

TECHNICAL FIELD

The invention concerns the field of in vitro culture of cells, tissues or organoids on culture plates and especially on multi-well plates. In particular, the invention concerns the control of the in vitro culture environment conditions in a confined space such as cell culture plates. More specifically, the invention concerns a method for the displacement of a fluid and simultaneously for the gas enrichment of a liquid cell culture medium and a system for controlling the in vitro cell culture environment on a multi-well cell culture plate.

Previous Technique

The in vitro culture of cells, or cell assemblies such as the culture of tissues, spheroids or even more recently of organoids, namely of three-dimensional multi-cell structures which reproduce in vitro the microanatomy of an organ, are increasingly used today as a tool for the toxicological evaluation of substances, especially pharmacological or cosmetic substances.

These in vitro models are used in particular in pharmaceutical research since they are a serious alternative to in vivo models, that is to say animal testing, against which economic and ethical pressures are emerging at international level.

Hence, in order to be able to carry out controlled medium and long-term biological experiments to analyse therapeutic compounds, cosmetics or any other potentially hazardous substances, it is essential to be able to control the cell culture parameters, especially the selective environmental changes induced and with automated monitoring of the activity of these confined cell environments.

Indeed, the preparation of high quality molecular and cell samples is important for various clinical, research and other applications. In vitro samples which have characteristics close to their in vivo characteristics can potentially benefit a wide range of molecular and cell applications. The manipulation, characterisation, culture and visualisation of cells or other biologically or chemically active materials (such as, for example, beads coated with various biological molecules) are increasingly appreciated in the fields of drug discovery, disease diagnosis and analysis, and various other therapeutic and experimental work.

Microfluidic cell culture, which is the culture of cells in chambers connected and supplied by microchannels characterised by fluidic volumes between 1 pL and 100 mL, is a major technology for drug testing, tissue culture, toxicity testing and biological research. It improves cell culture conditions, provides better quality cell data, and reduces reagent consumption and costs.

This automated microfluidic cell culture system for controlling the in vitro culture environment allows fine control of the cell culture conditions in order to get as close as possible to in vivo conditions. This system is a combination of perfused controlled mediums with appropriate chemical, biochemical and gas composition, and a controlled temperature. This microfluidic cell culture system guarantees the control of the shear stress of the cultured cells, and prevents the leakage of biological elements and/or sensitive and/or hazardous compounds and/or contamination of samples by foreign germs or undesirable particles when carrying out experimental protocols.

Today, the standard tool for analytical research and clinical diagnostic tests which is used in laboratories is the culture plate with several wells, called the multi-well culture plate. These multi-well plates have been used for many years for cell and tissue culture.

To protect the cell cultures from contamination by foreign germs or undesirable particles, the multi-well plates are closed by a matching lid. According to the type of cells or tissues growing in the wells, the cell culture medium must be changed regularly, to renew the nutrients and/or the treatment applied to the cells (Paul J.: Cell and Tissue Culture. 5th Ed., Edinburgh, 1975). The cell culture medium or the cell treatment is generally changed manually which not only takes a great deal of time but also involves a risk of contamination by foreign germs or undesirable particles from the external environment (Freshney R. I.: Animal Cell Culture: A Practical Approach. 2nd Ed. A.R. Liss, New York, 1987).

The current limits of use of these devices include the fact that long-term cell culture implies continuously exchanging and enriching the cell medium using methods which have numerous limitations depending on external factors limiting the continuous testing of biological material in controlled environment multi-well culture plates to just a few days.

Patent application WO 2009089189 (MILLIPORE CORPORATION) describes a microfluidic cell culture system consisting of, among other things, a microfluidic chamber improving the cell culture conditions. The pressurised displacement of the liquids to the microfluidic cell culture chamber provides high precision, even for very small volumes. The rapid laminar flow switching among five flow inlet solutions, as well as the perfusion barriers allow continuous mass transport without shear stress to the cells. In particular, this system allows analysis experiments to be performed on living cells for more than three days but not exceeding five days on the stage of any standard inverted microscope. This system also has dynamic control of the gas flow and temperature.

However, this system is not without disadvantages. Indeed, this system's high complexity results in a high failure rate of the manufactured device. The perfusion of the enrichment medium is obtained by diffusion, which limits the rapid enrichment with nutrients and also limits the dosing of the compounds to be tested. The gas enrichment of the cell medium is by diffusion through a porous material (such as the silicone elastomer Polydimethylsiloxane, PDMS) which also limits the efficiency and enrichening power of the gases and requires the use of materials which can potentially absorb the basic molecules studied for their effects, such as the pharmacological or cosmetic compounds present in the perfused medium. The system is not suitable for the culture of large biological assemblies such as tissue biopsies, due to its dimensions, and the culture time is limited to 3 days, with a maximum of 5 days.

In addition, this system is not totally compatible with the use of standard multi-well culture plates.

Finally, this system lacks flexibility to interconnect different cell cultures and provide perfused mediums in the plate or to choose different well configurations containing seeded cells.

Patent application WO2007092571 (WAFERGEN INC) describes a tissue culture device isolated from the environment and which can be used for cell culture. This tissue culture device consists of: a multi-well plate with a plurality of wells, in which each well is shaped to receive at least two insertable tubes, a first manifold for supplying nutrient elements and which consists of a plurality of individual well supply ducts, a manifold placed above the wells and aligned so that each well supply duct reaches a position adjacent to the bottom of a well, a second manifold for waste removal and consisting of a plurality of individual waste removal lines. This second manifold reaches a position adjacent to the bottom of the well, where the waste supply line reaches a point slightly above that of the well supply line.

In certain variants the wells may include orifices connecting the adjacent wells together, this allows the passage of materials between the individual wells of the plate.

A temperature controlled lid with inlets for gas diffusion is also described.

The ports (external inlet/outlet connection) can also contain one or more port opening/closing control valves.

This system has certain disadvantages, in particular the perfusion medium is supplied from the exterior (external actuators to directly displace the liquid).

The gas mixture is supplied from the exterior to enrich the mediums only by surface diffusion inside the well. The gas enrichment where gas is supplied to the wells by specific ports is not suitable to gas-enriched microfluidic devices.

The wastes are extracted to the exterior, independently of the fluid supply actuators.

Gases, perfused liquids and wastes are manipulated by independent external actuators, which increases the system's complexity.

The mixing takes place in a well by agitating the well towards the exterior or by introducing magnetic, mechanical stirrers, which potentially modifies the cell position conditions.

The manipulation of the liquids, reagents or mediums perfused inside is not totally confined or isolated and can potentially contaminate the multi-well plates and the external actuators, especially after use.

Hence, the currently available methods either do not provide adequate isolation from the exterior, or are limited with respect to their fluidic versatility and the interwell communication, or require external systems to manipulate reagents during the experimentation, or are unable to maintain the medium's gas enrichment, or generate shear forces and stresses on the cultured cells and on the cell assemblies, which greatly exceed the physiological levels.

Gas enrichment is generally difficult to achieve in microfluidic devices and other cell culture devices where the surface contact between the perfused liquid and the gas is low or nonexistent and where the diffusion mechanisms are not an efficient solution.

There is therefore a need for a highly versatile technique and device adaptable to the multi-well culture plate standard, but not limited to them, for confinement in cell culture environments which are highly controlled in terms of temperature, composition of the medium, gas enrichment and fluid displacement. There is also a need to isolate these controlled environments from the exterior within multi-well culture plates while allowing optical observation and selective communication between different confined wells on the multi-well plate when necessary.

DISCLOSURE OF THE INVENTION

The invention fulfils this need by proposing a method for the displacement of a fluid and simultaneously for the gas enrichment of a liquid cell culture medium.

According to the invention, the method comprises:
- the injection of a controlled volume of a gas or gas mixture into at least one pressure chamber by means of at least one gas flow controller. This injection is takes place through at least one gas inlet into a volume of liquid, the injection produces bubbling and agitates the volume of liquid cell culture medium.
- a build-up of gas or gas mixture due to buoyancy in a hermetic space formed by the volume of the liquid cell culture medium and said at least one pressure chamber, and
- a pressure increase in said at least one pressure chamber until a sufficient controlled pressure is reached of less than or equal to 10 bar. This increase produces a displacement of the volume of liquid cell culture medium by at least one fluid outlet connecting the volume of liquid cell culture medium to the exterior of said at least one pressure chamber.

In a variant, the pressure chamber can be, for example, an isolated reservoir, or individual isolated reservoir, also called a sealed or independent individual reservoir, namely a reservoir isolated from non-controlled exterior mediums. Hence, the method according to the invention enables a system to be created which is based on the regulated perfusion of mixtures, especially gases. This system is used not only in an installation comprising a multi-well culture plate, but also to displace a fluid, enrich and control the gas mixture of the fluids in all microfluidic installations by using the pressure bubble chamber principle to generate microfluidic flows.

Advantageously, the method according to the invention enables the gas enrichment of perfused mediums in a totally isolated environment for the biological samples and the mediums used.

Hence it is not necessary to use an incubator structure to guarantee the biological living conditions in the closed microfluidic or fluidic system according to the invention.

The method according to the invention enables a cell culture, a tissue or any other living matter to be maintained in a living condition by a precise control of the vital biological parameters such as the composition of the medium's nutrients, the gas mixture and the temperature, and enables a precise control of the shear stress of the cells by low perfusion flows to avoid compromising the viability.

It is important to be able to control the different gas flow rates in order to be able to give a flow percentage for each gas while continuing to produce the total flow so that the gas mixture can be modified in real time while producing the same desired quantity of gas and fluidic flow.

According to a particular aspect of the invention, said at least one injected gas is chosen from among $O_2$, $CO_2$, $N_2$ or their mixtures.

This method enables different gas concentrations to be recreated on the different cell mediums to better imitate the physiological and pathological conditions of the tissues, organoids, spheroids and cell cultures in the natural environment. Many other gases and gas mixtures can be used.

According to another aspect of the invention, the displacement of the volume of liquid cell culture medium by said at least one fluid outlet connecting the volume of liquid cell culture medium to the exterior of said at least one pressure chamber takes place to a microfluidic device.

In a variant, the volume of liquid can be replaced by a volume of gas or gas mixture when the total volume of liquid has been displaced. Advantageously, the method can thus be implemented by a system consisting of a series of pressure chambers arranged in series or in parallel with each other and in which a liquid and/or a gas, or any other type of fluid can be successively displaced from one chamber to another.

The invention also relates to a cell culture system. This cell culture system consists of:
- at least one pressure chamber containing a volume of liquid cell culture medium. In addition, this pressure chamber has at least one gas inlet and at least one fluid outlet connecting the volume of liquid cell culture medium to the exterior of said at least one pressure chamber; and
- at least one gas flow controller configured to inject through the gas inlet, into the volume of liquid cell culture medium, a controlled volume of gas or gas mixture into said at least one pressure chamber.

This system also implements the method according to the invention, as described previously.

According to another aspect of the invention, the system comprises several pressure chambers arranged in series or in parallel with each other and in which the fluid is successively displaced from on chamber to another.

According to another aspect of the invention, said at least one pressure chamber is formed by an individual isolated reservoir.

The cell culture system according to the invention is advantageously compatible with any type of disposable multi-well plates. These multi-well plates are a standard widely used in pharmaceutical, biotechnological and life sciences experiments.

Hence the cell culture system according to the invention is simple to use whatever the embodiment and can be easily adapted to any standard multi-well plates. The cells cultured in the multi-well plate are perfectly isolated from the exterior environment and the changes of nutrient medium and the treatment changes no longer require to be manipulated manually. The temperature and gas enrichment parameters are automatically controlled, which eliminates the need for an incubator.

The cell culture system according to the invention enables the fluids to be selectively displaced from one well to another to perfuse mediums, apply a compound to an assembly or a given cell culture or to enable the communication between different assembled cells or in non-organised cell cultures, to recreate multi-organoid communications in the biological systems.

All the operations performed guarantee the isolation of the compounds, mediums and biological entities tested from the gas and liquid injection control devices.

The system according to the invention enables the cell culture environments (or any biological entities: spheroids, tissues, organoids, extracellular matrix cells, hydrogel cells, etc.) to be controlled in real time like, for example, by controlling the perfusion of the culture mediums at given pressure/flow values and, on option, enables the liquid and temperature to be selected. The manipulation of the perfused reagents is entirely confined/isolated inside the device (complete system only) controlled by the application of external gas pressures or the fluidically isolated introduction of thermalisation liquids.

This system also allows microscope observation of living samples in real time during the experiment.

According to another characteristic of the invention, the cell culture system also comprises:
- a multi-well cell culture plate;
- a device designed to be adapted on the multi-well cell culture plate, this device comprises at least one microfluidic circuit (A) consisting of at least one microfluidic channel formed in at least one integrated microfluidic plate, this microfluidic circuit (A) goes from at least one connection orifice or at least one fluidic connection duct to a manifold. The manifold also includes at least one cavity, said at least one cavity forming with at least one well of the multi-well cell culture plate said at least one pressure chamber. In addition, the manifold includes at least one nozzle or at least one orifice or at least one duct, said at least one nozzle or at least one orifice or at least one duct extends said at least one microfluidic channel, and forms said at least one complete microfluidic circuit (A) when the device is combined with the multi-well cell culture plate.

According to another aspect of the invention, the device includes at least one other integrated parallel microfluidic circuit (B), independent of said at least one microfluidic circuit (A), said at least one other integrated parallel microfluidic circuit (B) has at least one microfluidic channel formed in at least one other parallel microfluidic plate independent of the microfluidic plate.

Different microfluidic channel plates can be placed in the device according to the invention in order to increase the control of the biological environment of the cell culture and of the fluids perfused on the device if necessary.

According to another characteristic of the invention, an injected fluid flows from said at least one connection orifice or said at least one fluidic connection duct into said at least one microfluidic circuit (A) to the manifold and to the multi-well cell culture plate.

Hence, a fluid (gas or liquid) is injected through at least one orifice or at least one fluidic connection duct and then flows through at least one microfluidic circuit to at least one nozzle or at least one orifice or at least one duct of the manifold. The fluid is thus sent to a chamber, called the pressure chamber, formed by a cavity or an empty space in the manifold and a well of the multi-well plate on which said device is adapted. In a variant, the fluid can simply be evacuated to the exterior of the device.

Hence, the introduction of a fluid (liquid or gas) from the nozzles or the orifices or the ducts to the wells of the multi-well plate containing liquid, up to a level closing said nozzles or orifices or ducts enables the pressure in the well to be increased and not only allows fluidic displacement through other nozzles or orifices or ducts present in the wells of the multi-well plate subjected to an external pressure less than the internal pressure of the well, but also by a bubble effect and associated agitation of the liquid to enrich, for example, the culture medium and/or the liquids present in the wells or injected into the microfluidic circuit.

According to another characteristic of the invention, an injected thermalisation liquid flows from said at least one connection orifice or said at least one fluidic connection duct into said at least one integrated parallel microfluidic circuit (B).

Advantageously, this fluid is fluidically isolated from the device's other microfluidic circuits.

Hence, it is possible to also integrate the temperature control of the biological cell culture environment by circulating one or more thermalisation solutions in the device according to the invention (isolated from the components tested, mediums and biological entities). It is also possible to maintain different parts of the multi-well plate at different temperatures guaranteeing the integrity of the samples and of the compounds for certain experiments (drugs are sometimes kept at lower temperatures before application).

LIST OF FIGURES

Other purposes, characteristics and advantages of the invention will emerge more clearly upon reading the following description of a particular embodiment, provided as a simple non-restrictive example, in relation to the figures, among which:

FIG. 1: diagrammatically illustrates an exploded view of the device's structure according to an embodiment of the invention;

FIG. 2: shows a diagrammatic exploded view of the device's structure according to another embodiment of the invention;

FIG. 3: shows a diagram of a cross-sectional view of a part of the device according to any embodiment of the invention in relation to FIGS. 1 and 2;

FIG. 4A: diagrammatically illustrates an exploded view of the device according to the embodiment shown in FIG. 2 with a multi-well plate;

FIG. 4B: illustrates a diagrammatical view of the device according to any embodiment in relation to FIGS. 1 and 2 with a multi-well plate;

FIG. 5: illustrates a view of a multi-well plate assembly with the device according any embodiment in relation to FIGS. 1 and 2 when connected to the external thermalisation gas and fluid flow controller and placed in a microscope for real-time imaging of the cells;

FIG. 6A: shows a diagram of an example of a pressure chamber implementing the method according to the invention.

FIG. 6B: shows a diagram of an example of a pressure chamber implementing the method according to the invention when it is connected to the device according to any embodiment in relation to FIGS. 1 and 2.

DETAILED DESCRIPTION OF THE EMBODIMENTS OF THE INVENTION

The general principle of the invention consists of confining and controlling the chemical, biochemical and physical properties in time and space, such that the shear stresses induced or the local temperatures, of the biological environments in the devices such as for example microfluidic devices and in the cell culture plates containing several wells, also called multi-well culture plates, by means of a specially designed device. The invention is useful for performing controlled biological testing in the fields of discovery and pharmacological and biotechnological testing, controlled cell differentiation, therapeutic and cosmetic testing, research and testing of compounds and customised testing, as well as in all life sciences experiments requiring a precise control of the environmental conditions of the cells, tissues or organoids.

More specifically, the invention simultaneously proposes to enrich a liquid, such as for example a cell culture medium, with gas while displacing it to a microfluidic device. This prior step for the gas enrichment of a culture medium enables, in particular, the cell culture conditions to be maintained in the long term.

Subsequently, for the purposes of simplification, "cell culture" is understood to mean a non-organised or organised cell culture, namely a cell assembly such as for example tissues, spheroids or organoids. These cells can for example be from animals, such as humans, mice, or plants.

"Multi-well plate" is understood to mean standard plates comprising at least six wells in which a specific nutrient culture medium, certain chemical or biochemical compounds, with the cell type studied is introduced, as well as cells to be cultured.

"Microfluidic" is understood to mean channels with cross sections between 1 $\mu m^2$ and 10 $mm^2$.

We now show, in relation to FIG. 1, the structure of the device, according to a first embodiment of the invention.

The device 100 with shape selected from among the cubic, rectangular shapes but preferably substantially parallelepiped-shaped comprises a lid 1, and a part called the manifold 5, comprising un series of nozzles or orifices or ducts forming the base of this device.

The lid 1 has, on two opposite edges, one or more connection orifice(s) 6 or fluidic connection duct(s) (not shown) for attaching at least one fluid connector CNT (not shown) from a gas flow controller externally supplying a fluid such as a gas or a liquid, for the external real time control of the fluid pressure and/or of its flow. This lid 1 can be entirely opaque or, in a variant, allow the passage of light in order to obtain a real-time optical image of the biological samples.

In this variant, on the external top surface of the lid 1, several zones 11 allow the passage of light and thus a visualisation by microscope or by other means necessary to obtain real-time images of the biological samples. The lid 1 preferably has a flat surface at least on its bottom face. It can be manufactured with different materials including, but not limited to, polymers such as PMMA (poly(methyl methacrylate)), COP, PS (polystyrene), PEEK (polyetheretherketone) or PC (polycarbonate).

A microfluidic panel 2 is then attached between the flat surfaces of the bottom part of lid 1 and the top part of a connecting plate 3 which guarantees the selective sealing of the microfluidic channels and structures. This microfluidic panel 2 is preferably made of double-sided adhesive tape, cut in order to define microfluidic channels connecting the different wells of the multi-well culture plate 7 (not shown) to the nozzles or orifices or ducts of the manifold 5 and to the corresponding connection orifices 6 or fluidic connection ducts of the lid 1. Alternatively, the microfluidic panel is constructed using a polymer bonding technique. This microfluidic panel 2 defines the gas or liquid fluidic connections of the microfluidic device 100.

In a variant, the device 100 can be embodied in different ways, for example the microfluidic panel 2 is constructed in the lid 1, then bonded or connected to connecting plate 3 or to attachment panel 4 or directly to the manifold.

Connecting plate 3 has a substantially flat surface and facilitates the attachment of microfluidic panel 2 to attachment panel 4 and guarantees the selective sealing of the microfluidic channels. Hence, the lid 1 can be attached by means of microfluidic panel 2, connecting plate 3 and attachment panel 4 to the manifold 5, and consequently create a fluidic device to be subsequently assembled to a multi-well plate 7 (not shown) in order to generate the complete fluidic structure. This sandwich structure and its variants are embodied to guarantee the correct assembly of the different parts into a microfluidic structure allowing selective communication with a controlled exterior gas supplier, the movement of the fluids between the wells of multi-well plate 7 (not shown) while avoiding undesirable contamination, and the external circulation of the liquids.

The surface of connecting plate 3 is preferably transparent for an application where light must pass from the upper transparent zones 11 of the lid 1 to the bottom of the wells of the multi-well plate 7 for microscope imaging for example. The materials used to manufacture the connecting plate 3 are preferably chosen from among the COP or COC composites, glass or other transparent materials. Connecting plate 3 is traversed by a plurality of orifices 31 enabling the microfluidic channels of microfluidic panel 2 to be connected to the corresponding channels 51 shown in FIG. 3 of the manifold 5.

In a variant, the device 100 can be embodied in different ways, for example a plate such as connecting plate 3 could be used between the lid 1 and the microfluidic panel 2.

To attach the lid assembly 1, microfluidic panel 2, connecting plate 3 to manifold 5, an attachment panel 4 preferably made of double-sided adhesive tape is used. This attachment panel 4 also allows good communication between the wells of the multi-well culture plate 7 through a plurality of orifices 41 connecting the microfluidic channels defined by microfluidic panel 2 to the nozzles or to the orifices or to the ducts 51 of the manifold 5. Orifices 41 are opposite orifices 31.

Alternatively, this attachment panel 4 can be eliminated and connecting plate 3 is then directly attached to the manifold 5. For example, the different elements are fixed together using a polymer bonding technique.

Manifold 5 is a structure made of a flexible material, like for example an elastomer material such as polyurethane or silicone, defining microfluidic nozzles or orifices or ducts 51 and a cavity or empty space 52 reaching a defined depth in the multi-well culture plate 7 while sealing a fluidic circuit A. This fluidic circuit A is defined by the microfluidic channels of microfluidic panel 2, orifices 31 of connecting plate 3, orifices 41 of attachment panel 4 and the nozzles or orifices or ducts 51 of the manifold 5. The flexibility of the manifold 5 facilitates the assembly of the device to the wells of the multi-well culture plate 7 and guarantees the sealing of the resulting structure.

Alternatively, the manifold 5 is a structure made of rigid material, like for example a polymer such as PMMA (poly (methyl methacrylate)), COP, PS (polystyrene), PEEK (polyetheretherketone) or PC (polycarbonate), defining microfluidic nozzles or orifices or ducts 51 and a cavity or empty space 52 reaching a defined depth in the multi-well culture plate 7, while sealing a fluidic circuit A. The device is assembled to the wells of the multi-well culture plate 7 and guarantees the sealing of the resulting structure, for example by means of one or more O-ring seals or equivalent structure, or even by bonding.

We now show, in relation to FIG. 2, the structure of the device, according to another embodiment of the invention.

In this particular embodiment, another microfluidic plate 8 designed to be independent and not connected to circuit A of microfluidic panel 2 is added in order to generate a variation of the original invention, in which a thermalisation solution, namely a liquid capable of transferring heat, is circulated to control the temperature of the device 200. An external device for automatically heating or cooling the liquid and pumping mechanisms is then necessary for real-time temperature control.

This microfluidic plate 8 can be created like the other fluidic plates 2 preferably using a double-sided tape defining microfluidic channels or by directly incorporating it in the structure of the lid 1. This microfluidic plate 8 is inserted between the lid 1 and microfluidic panel 2, which allows microfluidic panel 2 to be connected to the lid 1.

In a variant, the microfluidic plate 8 can be inserted in different ways and at different levels of the sandwich structure, as can be easily deduced.

A connecting plate 9 with substantially flat surface is used to facilitate the connection of microfluidic plate 8 and microfluidic panel 2 with the lid 1. Connecting plate 9 is preferably transparent and manufactured of materials chosen from among the COP, COC, glass or other transparent materials, for an application where the light must pass through the upper transparent zones 11 to the bottom of the wells of the multiple plate 7 through the cavity or the empty space 52 (FIG. 3) for microscope imaging for example. In a variant, the connecting plate 9 also comprises orifices 91 allowing the microfluidic channels of plate 8 to be connected to certain orifices 31 and 41 in order to connect certain microfluidic nozzles or orifices or pipes 51 to the microfluidic channels of plate 8. Hence, a second parallel microfluidic circuit B independent of that formed by panel 2 can be created. This parallel circuit B enables, in particular, the temperature of the multi-well plate 7 to be regulated.

In a particular embodiment, the microfluidic plate 8 is dependent on microfluidic panel 2 and the microfluidic circuits A and B are also dependent or independent.

As a variation, one or more thermalisation fluid(s) with externally controlled temperature can be sent into different or similar selected parallel microfluidic channels in order to regulate the temperature of all the wells of the multi-well plate. In another variation, the temperature of certain selected wells only is regulated by the injection of one or more thermalisation liquid(s) into selected microfluidic channels. In another variant, specific fluids are integrated to perfuse the thermosetting solutes and control the temperature(s) of the device or of certain parts of the device.

As a variation of the two previous embodiments, hydrophobic filters separating the gas and liquid phases can be installed on the gas inlets and outlets, thus preventing the entry of liquid into the device or the exit of liquid from the device according to the invention and from the multi-well plate 7 once assembled.

In another variant, the structure of the device according to the embodiment in relation to FIG. 1 or 2 comprises a sandwich assembly of a stack microfluidic panels 2 or 8 with equal or different microfluidic structures alternating with connecting plate 3 or 9 for more complex or alternatively three-dimensional microfluidic circuit designs.

In a variant, the device comprises orifices or ducts for the selective recovery of fluids during the device's operation (for the purposes of analytic sampling).

In another variant, detection and biodetection devices are integrated in the device according to the invention for the real-time analysis of the sample, the perfused fluids or the resulting fluids (these devices can be of any type: electric, optical, mechanical, or other). These devices can, for example, control different parameters of the associated experiments (pH, temperature, potassium, electricity, etc.)

Elements 1 to 5 in the embodiment of FIG. 1, or 1 to 9 in the embodiment of FIG. 2 must be permanently assembled to form the device according to the invention.

The device according to the invention is then mounted on the top part of the standard multi-well culture plate 7, as subsequently shown in relation to FIGS. 4A to 4B and compressed by external means, so that the system device according to the invention with the multi-well culture plate 7 is completely sealed, except for the connecting orifices 6 or the fluidic connecting ducts.

We show in relation to FIG. 3 a diagram of a cross-sectional view of the structure of the manifold 5 of the device according to any embodiment in relation to FIGS. 1 and 2.

The manifold 5 consists of a substantially parallelepiped shaped flat surface 54 covering connecting structures 53 comprising microfluidic nozzles or orifices or ducts 51, with a cavity or an empty space 52. The cavity or empty space 52 can for example be substantially cylindrical, parallelepiped or cube shaped.

The flat surface 54 comprises orifices 511 for connecting the microfluidic channels of panels 2 and/or 8 to the microfluidic nozzles or orifices or ducts 51. The orifices 521 allow the passage of light to the bottom of the well when microscope imaging is necessary.

We now show, in relation to FIGS. 4A to 4B, an example of assembly of the device according to any embodiment in relation to FIGS. 1 and 2 on a multi-well plate.

FIG. 4A shows an exploded diagram of an assembly of the device 200 on a multi-well plate 7.

FIG. 4B shows an assembly diagram of the device according to any embodiment in relation to FIGS. 1 and 2 on a multi-well plate 7.

Before this assembly, the samples are placed in the multi-well plate 7, along with the reagents, before closing it with the assembled device. The mediums, samples, cell cultures and reagents are placed in the wells of the multi-well plate before the experiment (as is currently the case in pharmaceutical, biotechnological and biological laboratories) and remain isolated throughout its use after the assembly of the device according to the invention.

In a variant, one or more compound(s) are selectively perfused in independent individual wells or reservoirs.

When assembled, the two parts are sealed and connected to the exterior only by the connecting orifices 6 or by fluidic connecting ducts. The reagents and the biological samples are completely isolated from the exterior since the orifices are used either to circulate the fluids, gas or liquid (which are preferably prefiltered to prevent contamination). The thermalisation solutions flowing in independent microfluidic circuits must never come in contact with the reagents or the biological samples.

In a variant, the device comprises one or more microfluidic nozzles or orifices or ducts 51 with different heights to control—in combination with the given gas pressures and/or flows—which liquid is perfused in the reservoir(s) which contain the biological material. These microfluidic nozzles or orifices or ducts 51 are designed to control, over time, the selective application of a given dose of specific compounds such as drugs or toxic particles mixing with the usual life-sustaining mediums for the biological material.

Figures 1, 2:
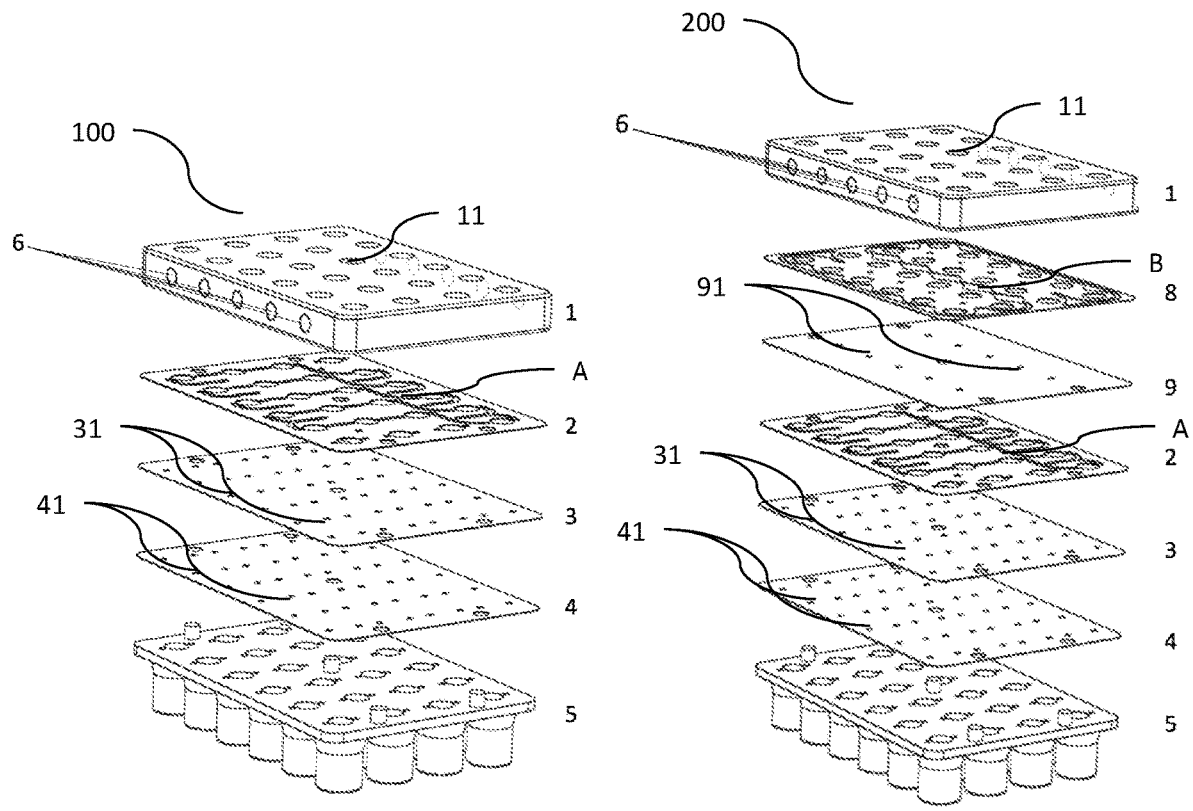
Figure 3:
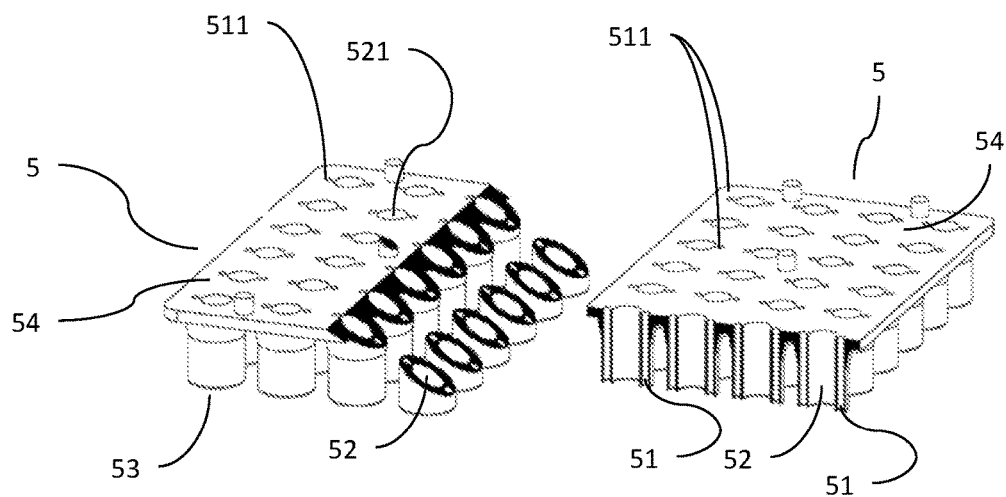
Figure 5:
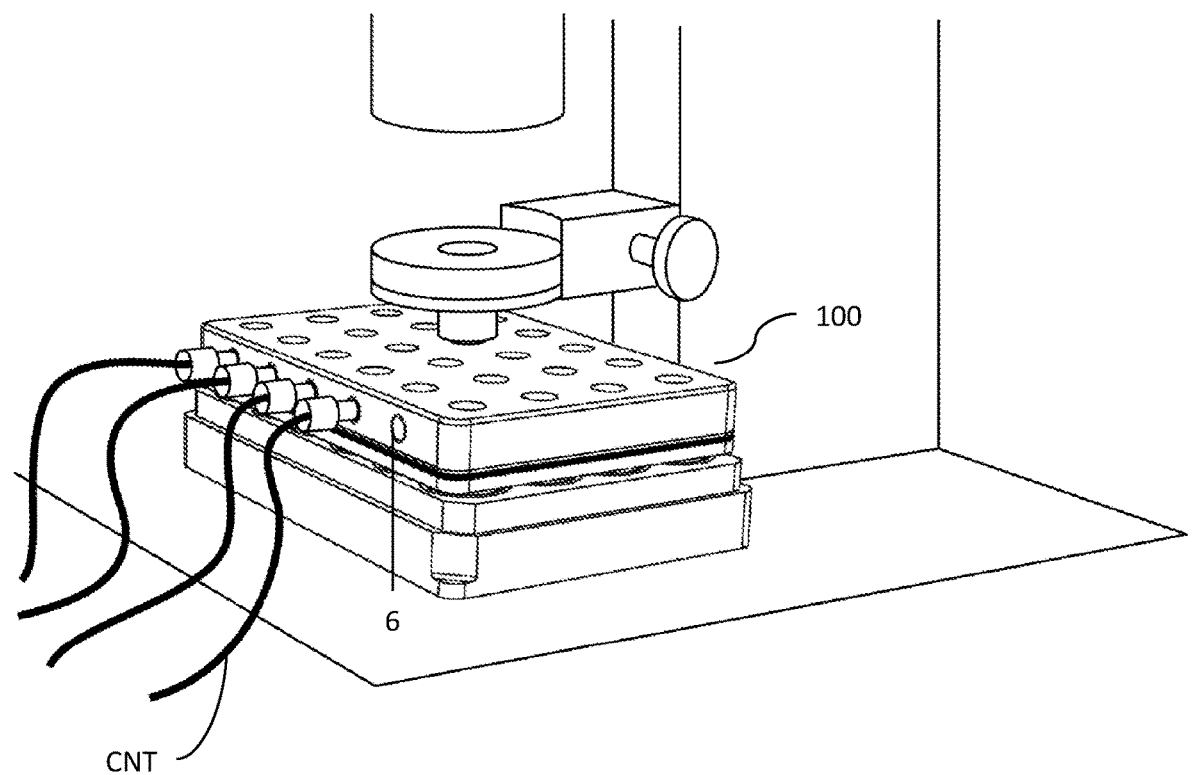

We now show, in relation to FIG. 5, the device according to any embodiment in relation to FIGS. 1 and 2 assembled to a multi-well culture plate charged with reagents and biological material, when connected to the external thermalisation gas and fluid flow controller and placed in a microscope for real-time imaging of the cells.

FIG. 5 shows an installation controlled by a computer-controlled gas or gas mixture pressure and/or flow control system and observed using an inverted microscope for example. The installation comprises, among other things, the device assembly 100 or 200 according to the invention with the multi-well plate 7, as well as an external gas supply with real-time control of the mixture of several gases (not shown), a real-time precise flow and/or pressure regulator (not shown) to regulate the flow of gas or gas mixture, one or more connector(s) CNT for the application of fluid, gas or liquid, or of a controlled gas mixture with different percentages of $O_2$, $CO_2$ and $N_2$ controlled in real time, for example.

In the installation, the temperature of the microscope stage is also controlled to maintain the correct temperature at the bottom of the assembly to guarantee the survival of the cells over long periods of time.

In an alternative configuration, the temperature is entirely controlled by the thermalisation solution which flows through the device according to the invention.

Figure 6A:
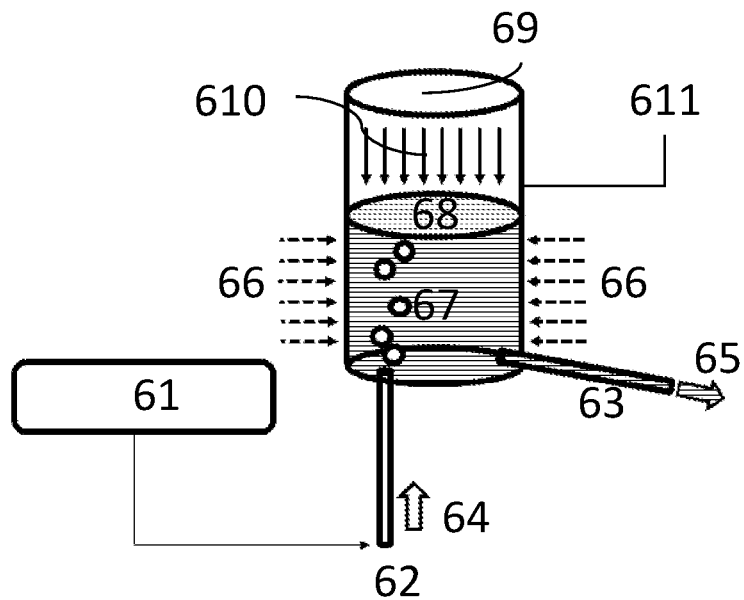
Figure 6B:
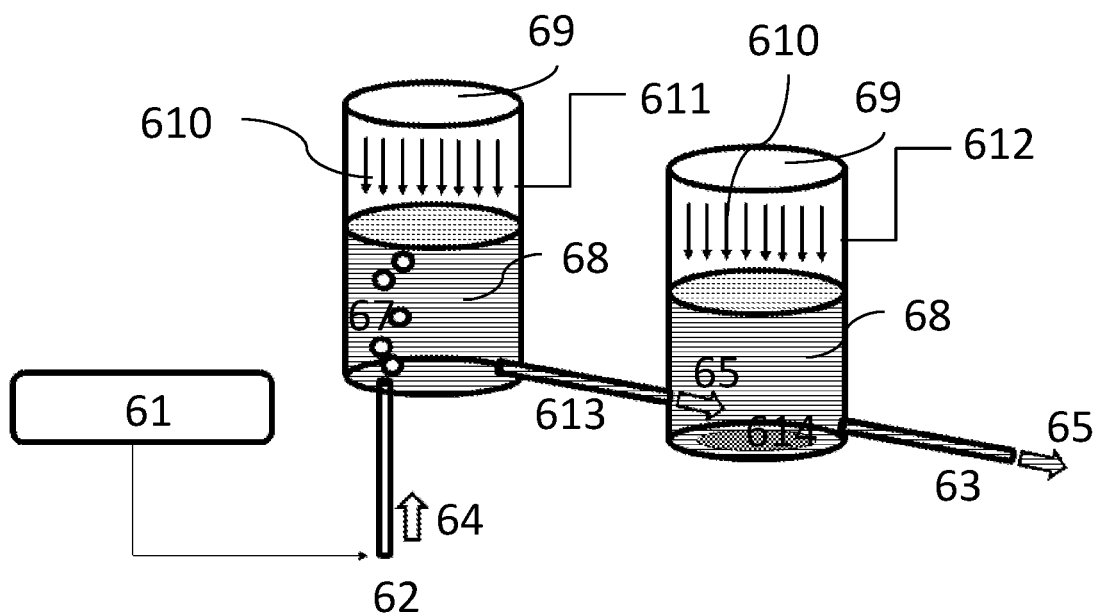

We now show, in relation to FIGS. 6A and 6B, a diagram of an example of a pressure chamber implementing the method according to the invention (FIG. 6A) when it is associated with a gas flow controller. In a particular embodiment of the invention, it can also be connected to the device according to any embodiment in relation to FIGS. 1 and 2 (FIG. 6B).

"Pressure chamber" is understood to mean, for example, an isolated reservoir which could be connected to any device and more specifically to any microfluidic device for the purposes of the invention, and which can, if necessary, be associated with a gas flow controller, or else the device according to the invention can be associated with a multi-well plate by means of an adaptive device designed for this purpose such as that described in this invention. The pressure chamber is then formed in this case by the manifold 5 and the well of the plate when the device is placed on and seals the multi-well plate 7. In another example, one of more isolated reservoir(s) forming a pressure chamber can be mounted in series or in parallel with one or more devices according to the invention.

In particular, FIG. 6A shows a diagram of the method for controlling the displacement and gas enrichment of a perfused cell medium for the long-term culture of tissues, cells, spheroids or organoids in closed hermetic devices. This method can be implemented by microfluidic chips, reservoirs isolated from non-controlled exterior mediums can for example be associated with a gas flow controller or even in multi-well plates sealed with a device according to the invention with their wells isolated from non-controlled exterior mediums. This method can also be implemented by a system comprising, on the one hand, an isolated reservoir, also called a pressure chamber, associated with a gas flow controller.

A gas and/or gas mixture flow controller 61, also called a gas flow controller, allows the gas composition, gas flow and the pressure of the gas or gas mixture to be controlled.

A gas or gas mixture is injected through a gas inlet 62 which takes the form of an orifice or a duct for the injection into the sealed reservoir, also called the pressure chamber 611, in a volume of liquid 68 contained in this chamber. The sealed reservoir has a given number of gas inlets 62 and fluid outlets 63. The volume of liquid 68 can be, for example, a cell culture medium, a treatment, etc. The direction of the gas flow 64 is from the gas flow controller 61 to the volume of liquid 68.

As the gas is being injected, gas bubbles 67 rise towards the volume of gas 69 through the volume of liquid 68, disturbing the liquid and facilitating the mixing of the liquids and the absorption of the gases. The volume of gas 69 is sealed by the liquid 68 and the reservoir (or pressure chamber) 611. The volume of liquid 68 and the reservoir (or pressure chamber) 611 thus form a hermetic space. The pressure in the pressure chamber 611 increases due to the buoyancy of the gas, thus forming a backpressure 610 produced by the gas build-up in the volume of gas 69 and pushing the volume of liquid 68. The pressure thus increases until it reaches a sufficient controlled pressure of less than or equal to 10 bar.

This volume of liquid is then evacuated through a fluid outlet 63, which takes the form of an orifice or a duct, the fluid can initially be a liquid then, when the liquid has been evacuated, a gas. The direction 65 of the liquid, or of the gas when there is no longer any liquid in the pressure chamber, is from the pressure chamber 611 to the exterior of the chamber.

In a variant, an external heating and/or cooling system 66 is used to regulate the temperature of the pressure chamber 611. This system can de designed to provide an additional liquid convection in the reservoir, thus facilitating the gas enrichment and the agitation of the liquid.

FIG. 6B shows a diagram of an example of a pressure chamber implementing the method according to the invention when it is connected to the microfluidic device according to any embodiment in relation to FIGS. 1 and 2. In particular, FIG. 6B shows a diagram of a method for displacing a real-time controlled quantity of cell culture medium enriched with a real-time controlled gas mixture for the long-term culture of biological material (where the long term is between 1 day and 60 days) in closed hermetic devices such as microfluidic chips, reservoirs isolated from non-controlled external environments, or multi-well plates sealed by the device according to the invention with their wells isolated from non-controlled external environments.

In this embodiment, the volume of liquid 68 is evacuated to a fluid inlet 613 of a sealed reservoir 612 which has a given number of fluid inlets 613 and fluid outlets 63, taking the form of an orifice or a duct. In this reservoir 612, biological material 614 such as, for example, cells, tissues, organoids or spheroids is cultured. The pressure in the reservoir 612 increases forming a backpressure 610 which pushes on the volume of liquid 68 which is then evacuated to outlets 63 in direction 65.

This perfusion system is based on pressurised chambers 611 or 612 with openings immersed in a liquid medium (at least two from any side, from the lower or upper part) which can be used selectively in order to supply a controlled gas composition to simultaneously selectively enrich the medium by pushing it and agitating it due to bubble effect and build up (pressure formation) in an upper space of the gas medium. In other words, the forced increase in the gas pressure in the pressure chamber 611, 612 enriches the culture medium with gas due to gas bubble effect on the liquid while displacing the liquid in the desired direction at the same time.

All the fluidic operations and the gas enrichment operations are performed by controlling the pressure and/or flow of the fluid (gas) and/or of the fluid mixture (gas mixture) applied at the different gas inlets 62.

What is claimed is:

1. A cell culture system, which comprises:
   at least one pressure chamber adapted to contain a volume of liquid cell culture medium, said pressure chamber comprising at least one gas inlet and at least one fluid outlet to connect said volume of liquid cell culture medium to an exterior of said at least one pressure chamber;
   at least one flow controller configured to inject, through said gas inlet into said volume of liquid cell culture medium, a controlled volume of gas or gas mixture into said at least one pressure chamber;
   a multi-well cell culture plate; and
   a microfluidic device adapted to said multi-well cell culture plate, comprising:
      a lid having at least one connection orifice or at least one fluidic connection duct for attaching at least one fluid connector from the flow controller,
      a manifold comprising at least one cavity, said at least one cavity forming with at least one well of said multi-well cell culture plate said at least one of pressure chamber, and at least one nozzle or at least one orifice or at least one duct,
      a microfluidic panel defining at least one microfluidic channel,
      said microfluidic panel connecting said at least one well of the multi-well culture plate to the at least one nozzle or orifice or duct of said manifold and to the corresponding at least one connection orifice or fluidic connection duct of said lid, a microfluidic circuit being formed when said microfluidic device is combined with said multi-well cell culture plate.

2. The cell culture system according to claim 1, wherein said flow controller is configured to inject the controlled volume of a gas or gas mixture into said volume of the liquid cell culture medium so as to, when the at least one pressure chamber contains the volume of liquid cell culture medium:
   produce bubbling and agitation of said volume of liquid cell culture medium;
   build-up said gas or gas mixture due to buoyancy in a hermetic space formed by said volume of liquid cell culture medium and said at least one pressure chamber, and
   increase pressure in said at least one pressure chamber until a sufficient controlled pressure is reached of less than or equal to 10 bar, said increasing pressure producing a displacement of said volume of liquid cell culture medium through the at least one fluid outlet connecting said volume of liquid cell culture medium to the exterior of said at least one pressure chamber.

3. The cell culture system according to claim 1, wherein said system comprises several pressure chambers mounted in series or in parallel with each other and in which fluid is successively displaced from one chamber to another.

4. The cell culture system according to claim 1, wherein said at least one pressure chamber is formed by an isolated individual reservoir.

5. The cell culture system according to claim 1, wherein said device comprises at least one other integrated parallel microfluidic circuit, independent of said at least one microfluidic circuit, said at least one other integrated parallel microfluidic circuit having at least one microfluidic channel formed in at least one other parallel microfluidic plate independent of said microfluidic plate.

6. The cell culture system according to claim 1, arranged so that an injected fluid flows from said at least one connection orifice or said at least one fluidic connection duct into said at least one microfluidic circuit to said manifold and to said multi-well cell culture plate.

7. The cell culture system according to claim 5, arranged so that an injected fluid flows from said at least one connection orifice or said at least one fluidic connection duct into said at least one other integrated parallel microfluidic circuit.

8. The cell culture system according to claim 5, arranged so that an injected thermalisation liquid flows from said at least one connection orifice or said at least one fluidic connection duct into said at least one other integrated parallel microfluidic circuit.

9. A cell culture system, which comprises:
at least one pressure chamber adapted to contain a volume of liquid cell culture medium, said pressure chamber comprising at least one gas inlet and at least one fluid outlet to connect said volume of liquid cell culture medium to an exterior of said at least one pressure chamber; and
at least one flow controller configured to inject, through said gas inlet into said volume of liquid cell culture medium, a controlled volume of gas or gas mixture into said at least one pressure chamber,
wherein said flow controller is configured to inject the controlled volume of a gas or gas mixture into said volume of the liquid cell culture medium so as to, when the at least one pressure chamber contains the volume of liquid cell culture medium:
produce bubbling and agitation of said volume of liquid cell culture medium;
build-up said gas or gas mixture due to buoyancy in a hermetic space formed by said volume of liquid cell culture medium and said at least one pressure chamber, and
increase pressure in said at least one pressure chamber until a sufficient controlled pressure is reached of less than or equal to 10 bar, said increasing pressure producing a displacement of said volume of liquid cell culture medium through the at least one fluid outlet connecting said volume of liquid cell culture medium to the exterior of said at least one pressure chamber.

10. The cell culture system according to claim 9, wherein said system comprises several pressure chambers mounted in series or in parallel with each other and in which fluid is successively displaced from one chamber to another.

11. The cell culture system according to claim 9, wherein said at least one pressure chamber is formed by an isolated individual reservoir.

12. The cell culture system according to claim 9, wherein said device comprises at least one other integrated parallel microfluidic circuit, independent of said at least one microfluidic circuit, said at least one other integrated parallel microfluidic circuit having at least one microfluidic channel formed in at least one other parallel microfluidic plate independent of said microfluidic plate.

13. The cell culture system according to claim 9, arranged so that an injected fluid flows from said at least one connection orifice or said at least one fluidic connection duct into said at least one microfluidic circuit to said manifold and to said multi-well cell culture plate.

14. The cell culture system according to claim 12, arranged so that an injected fluid flows from said at least one connection orifice or said at least one fluidic connection duct into said at least one other integrated parallel microfluidic circuit.

15. The cell culture system according to claim 12, arranged so that an injected thermalisation liquid flows from said at least one connection orifice or said at least one fluidic connection duct into said at least one other integrated parallel microfluidic circuit.

* * * * *